US010869625B2

(12) United States Patent
Leichner

(10) Patent No.: US 10,869,625 B2
(45) Date of Patent: Dec. 22, 2020

(54) SAMPLING DEVICE AND SYSTEM FOR COLLECTING A BODY FLUID SAMPLE

(71) Applicant: Roche Diabetes Care, Inc., Indianapolis, IN (US)

(72) Inventor: Wilhelm Leichner, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 157 days.

(21) Appl. No.: 15/717,253

(22) Filed: Sep. 27, 2017

(65) Prior Publication Data

US 2018/0085041 A1 Mar. 29, 2018

(30) Foreign Application Priority Data

Sep. 28, 2016 (EP) ..................... 16191038

(51) Int. Cl.
*A61B 5/157* (2006.01)
*A61B 5/15* (2006.01)
(Continued)

(52) U.S. Cl.
CPC ............ *A61B 5/157* (2013.01); *A61B 5/1477* (2013.01); *A61B 5/14532* (2013.01); *A61B 5/150022* (2013.01); *A61B 5/15045* (2013.01); *A61B 5/15107* (2013.01); *A61B 5/15113* (2013.01); *A61B 5/15144* (2013.01); *A61B 5/15194* (2013.01); *A61B 5/150358* (2013.01); *A61B 5/150419* (2013.01); *A61B 5/150519* (2013.01)

(58) Field of Classification Search
CPC ... A61B 5/157; A61B 5/14532; A61B 5/1477; A61B 5/150022; A61B 5/150358; A61B 5/150419; A61B 5/15045; A61B 5/150519; A61B 5/15107; A61B 5/15113; A61B 5/15144; A61B 5/15194
USPC .......................................... 600/573
See application file for complete search history.

(56) References Cited

U.S. PATENT DOCUMENTS

2006/0167382 A1   7/2006  Deshmukh
2010/0168617 A1*  7/2010  Fuerst ................ A61B 5/15142
                                                      600/583
(Continued)

FOREIGN PATENT DOCUMENTS

EP     1 518 509 A1    3/2005
EP     2 030 566 A1    4/2009
(Continued)

OTHER PUBLICATIONS

English Translation of European Search Report, EP Application No. 16191038.5, dated Mar. 14, 2017, 8 pages, Germany.

*Primary Examiner* — Daniel L Cerioni
(74) *Attorney, Agent, or Firm* — Bose McKinney & Evans LLP

(57) ABSTRACT

This disclosure concerns a sampling device and a system for collecting body fluid, comprising a metal lancing unit having a distal tip suitable for piercing skin and a capillary channel extending between the tip and a proximal section of the lancing unit for collecting body fluid; and further comprising a plastic holding unit affixed to the lancing unit for manipulating the lancing unit in order to form an incision in the skin, wherein the holding unit contains a sorbent adapted for sorption of moisture and/or volatile substances to protect the sampling device from degradation prior to use.

19 Claims, 1 Drawing Sheet

(51) Int. Cl.
*A61B 5/151* (2006.01)
*A61B 5/145* (2006.01)
*A61B 5/1477* (2006.01)

(56) References Cited

U.S. PATENT DOCUMENTS

2011/0040316 A1* 2/2011 Pottala ............... A61B 5/15142
606/182
2011/0060246 A1* 3/2011 List ..................... A61B 5/1405
600/583
2011/0077554 A1 3/2011 Roe et al.

FOREIGN PATENT DOCUMENTS

| WO | WO 2008/145625 A2 | 12/2008 |
| WO | WO 2012/126945 A1 | 9/2012 |

* cited by examiner

SAMPLING DEVICE AND SYSTEM FOR COLLECTING A BODY FLUID SAMPLE

RELATED APPLICATIONS

This application claims priority to EP 16 191 038.5, filed Sep. 28, 2016, the entire disclosure of which is hereby incorporated herein by reference.

BACKGROUND

This disclosure relates to a sampling device for collecting a sample of a body fluid comprising a metal lancing unit having a distal tip suitable for piercing skin and a capillary channel extending between the tip and a proximal section of the lancing unit for collecting body fluid; and a plastic holding unit affixed to the lancing unit for enabling movement of the lancing unit in order to form an incision in the skin. This disclosure further concerns a sampling system including such a disposable sampling device.

In contrast to simple test strips for self-determination of blood glucose by patients, so-called integrated sampling devices and systems pursue a highly sophisticated concept of sample collection and analyte detection in one step in order to achieve an outstanding use convenience. Hitherto, integrated samplers have not reached the market, not only due to economic reasons. Due to the contamination with sample and the irreversible detection chemistry, the samplers have to be construed as low-cost disposables only for single use. Specific problems are caused by ambient influences which may lead to degradation during storage, in particular, due to substances permeating or emanating from containers and interfering capillary action or detection means. Other problems are due to engagement of metallic structures during motion sequences which over the time may lead to abrasion and obstruction of driving elements.

SUMMARY

On this basis, this disclosure further improves the known devices and systems and provides a design which improves functional stability and safety while avoiding malfunction of actuated parts.

This disclosure is based on the idea of providing a sampling device with an improved multifunctional component. Thus, it is proposed according to this disclosure that the holding unit contains a sorbent material adapted for sorption of moisture and/or volatile substances to protect the device from degradation prior to use. The plastic holding unit allows for easy integration of the sorbent to protect the individual sampling device. In particular, the sorbent may help to maintain the hydrophilicity of the capillary channel and to avoid moisture-induced degradation of a test chemistry that may be arranged on the device. Furthermore, the holding unit being made of a plastic material does not only allow for cost-effective production of a handling means, but also reduces abrasion of metal parts of an engaging actuation mechanism, also referred to as "actuator".

The term "volatile substances" as used within the present application comprises substances which have a vapor pressure of $\geq 0.1$ kPa at a temperature of 20° C. Typical examples of volatile substances in the sense of the present application are hydrophobic, organic chemical substances having a molecular weight between 100 and 1000 Daltons.

Advantageously, the sorbent is selected from the group consisting of carbon black, activated carbon, graphite, desiccant polymers, silica gel, zeolites, ion exchange resins, molecular sieve materials. This allows to adsorb or absorb a variety of interfering substances, in particular moisture from the ambient air and monomers released from containers and the like.

For further improvement it is advantageous when the sorbent is dispersed in the material of the holding unit or disposed therein or coated thereon.

Another manufacturing improvement is achieved when the holding unit is formed as an injection molded component from a molding composition containing the sorbent.

According to a preferred implementation, the holding unit comprises a plastic structure adapted for releasable engagement of an actuation mechanism. Thus, while avoiding scratches or abrasion on metallic structures, the function of a metal actuator can be retained over time.

Another improvement provides that the plastic structure is formed as a hole or a recess in the holding unit.

The lancing unit can be formed from an elongate piece of a flat material, in particular from a sheet of stainless steel.

For further improvement of liquid sample-uptake, the capillary channel can be provided as a groove or slit which is laterally open to the outside on one side or on two opposite sides.

A particular embodiment further comprises a test element adapted for detecting at least one analyte in the body fluid and arranged to receive body fluid via the capillary channel. Thereby, the sample can be analyzed "on-board" without significant delay.

According to another implementation, the test element is supported between the holding unit and the lancing unit in fluidic connection to the capillary channel. In this configuration, the test element is maintained in direct vicinity of the sorbent, and the test chemistry thereon may even support the suction of sample by capillary action.

For further design improvement it is advantageous when the test element is retained on a surface area of the holding unit and the surface area confines a measuring window for an optical detection of the analyte.

For providing a functional final product, it is advantageous when the holding unit is fixedly connected to a proximal part of the lancing unit by means of form-locked connecting elements, in particular by riveted pins.

Another aspect of this disclosure concerns a sampling system for collecting a sample of a body fluid comprising at least one sampling device according to the disclosure and further comprising an actuation mechanism which is operable to drive a lancing movement of the lancing unit, wherein the actuation mechanism comprises a metallic driving member adapted to engage a plastic structure of the holding unit. In this way, the advantages elucidated above are achieved in analogues way within an instrument adapted for use of disposable devices preferably provided in a magazine.

The metallic driving member can be formed by a gripper or hook, such that gripping and movement of individual sampling devices is simplified.

In this connection it is also advantageous when the plastic structure is provided as a hole or a recess in the holding unit.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
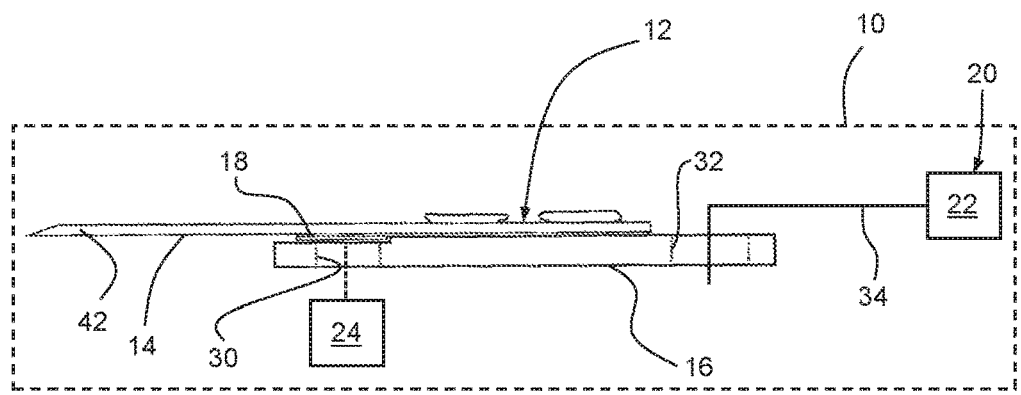
FIG. 1 is a schematic view of a sampling system comprising an integrated microsampler for collecting and measuring body fluid.

FIG. 1 shows a sampling system 10 provided for collection of a sample of a body fluid (e.g. blood) and detection of at least one analyte (e.g. glucose) in the body fluid. The system 10 comprises at least one disposable sampling device (integrated microsampler 12) consisting of a metal lancing unit 14, a plastic holding unit 16 and a test element 18. The system 10 further comprises a preferably portable meter 20 including an actuation mechanism 22 for a reciprocating lancing movement of the microsampler 12 in and out the skin of a user and a measuring unit 24 for a reflectometric optical measurement on the test element 18.

Figure 2:
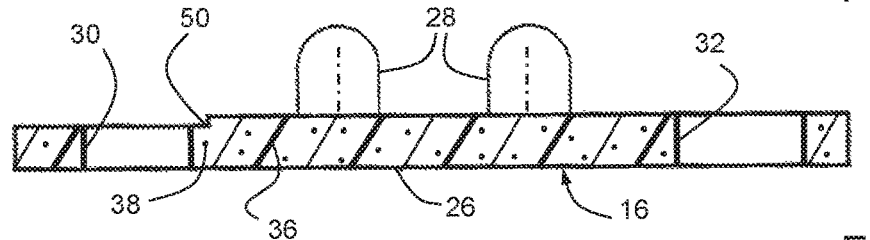
FIG. 2 is a sectional view of a plastic holding unit of the microsampler.
Figure 3:
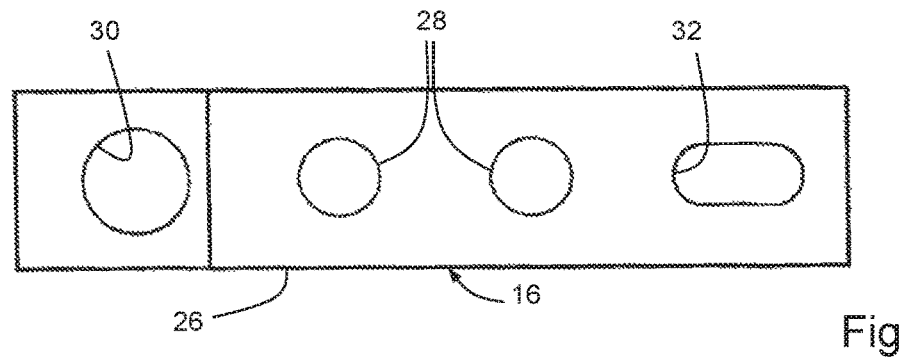
FIG. 3 is a top view of the holding unit of FIG. 2.

As shown in more detail in FIGS. 2 and 3, the holding unit 16 comprises a flat base part 26 having a rectangular outline. On a central section, two upright pins 28 are molded thereon at a distance from each other. In the distal section, a through-hole is provided as a measuring window 30. The proximal section comprises an oblong hole 32 which allows engagement of a metallic hook 34 of the actuation mechanism 22.

The holding unit 16 is formed as an injection molded component from a molding composition which contains a thermoplastic base material 36 and a sorbent material 38 for sorption of moisture and/or volatile substances to protect the microsampler 12 from degradation prior to use. For example, carbon black may be dispersed in the molding composition.

Figure 4:
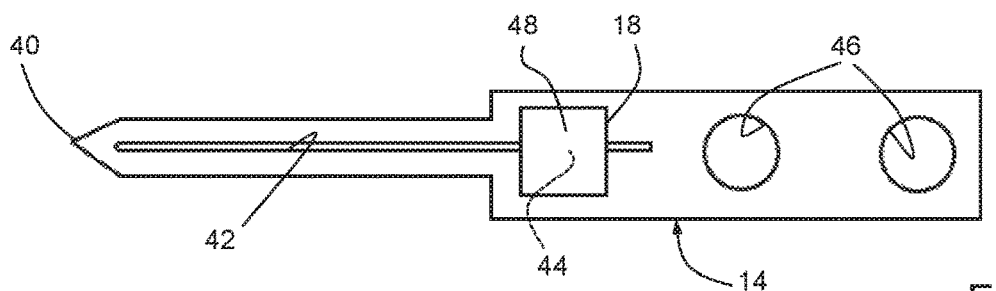
FIG. 4 is a bottom view of a metal lancing unit of the microsampler including a capillary channel.

FIG. 4 shows the lancing unit 14 as a separate part prior to assembly with the holding unit 16. The lancing unit 14 is formed from a sheet of stainless steel by chemical milling or edging. Further details of such a manufacturing process may be found in EP-A 1671585, which is incorporated by reference herewith.

As further apparent from FIG. 4, the lancing unit 14 is provided with a sharp tip 40 at its distal end, i.e. the end pointing to the skin in use. In this way, an incision can be formed in the skin in order to collect the body fluid. A capillary channel 42 in the lancing unit 14 allows to transport a small amount of body fluid from the tip to a proximal sampling section 44. For this purpose, the capillary channel 42 extends in the longitudinal direction of the elongate lancing unit 14 and is formed as a groove which is laterally open on the bottom side of the lancing unit 14. It is conceivable that the capillary channel is widened in the sampling section 44. The depth of the groove may be in the range of 50 to 80 μm.

In order to support the liquid uptake and transport, the capillary channel 42 may be coated with a hydrophilic agent or with a suspension containing nanoparticles.

Such nanoparticles may comprise particles having a silicon dioxide structure as described in the claims of WO 2012/126945.

Examples of hydrophilic agents are
non-ionic tensides, such as polysorbate,
hydrophilic metal oxides, e.g. AlOOH, $TiO_x$, $SiO_2$,
organic polymeric compounds, such as PVP-PEG,
water-soluble organic polyacids or salts thereof, such as polyacrylic acid or heparin salts, dextran sulfate, chondroitin sulfate.

For a defined form-locking connection to the pins 28 of the holding unit 16, two separate holes 46 are provided on the lancing unit 14 at a distance in the longitudinal direction thereof.

Further depicted in FIG. 4 is the test element 18 which is arranged in fluid connection with the sampling section 44 of the capillary channel 42. The test element 44 consists of a pad 48 coated with a dry test chemistry which is responsive to the analyte by an irreversible color change.

Figure 5:
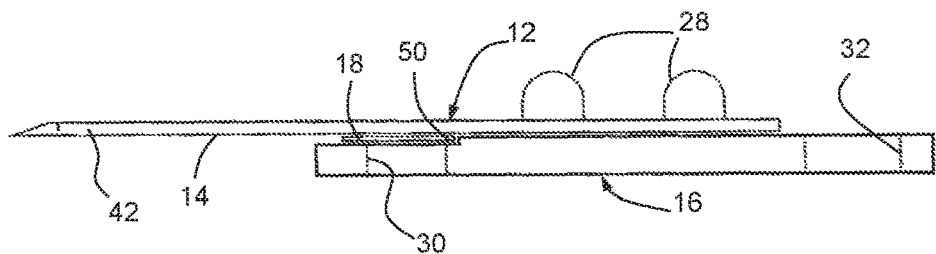
FIG. 5 is a side view of the holding and lancing unit in a pre-assembled state.

FIG. 5 shows the microsampler 12 in a pre-assembled state where the pins 28 reach through the holes 46 and the bottom side of the lancing unit 14 rests flat on the top side of the holding unit 16. Then, in order to provide for a firm connection, the heads of the pins 28 are pressed flat to provide a riveted joint, as shown in FIG. 1.

As further illustrated in FIG. 5, the test element 18 is arranged on a surface area 50 of the holding unit 16 which confines the measuring window. Thus, the body fluid is supplied from the capillary channel 42 to the top side of the test pad 48, whereas the optical measurement can be performed through the window 30 on the rear side of the test pad 48.

In this configuration, the sorbent material 38 of the holding unit 16 adsorbs interfering substances during storage of the microsampler 12. Such substances may include moisture which would disturb the dry setting of the reactive chemistry on the test pad 48. Furthermore, the sorbent material 38 may be furnished to adhere monomers emitted by a container of the microsampler which could lead to a degradation of the hydrophilic properties of the capillary channel 42.

In use, the microsampler 12 is ejected in distal direction out of a guiding chamber of the meter 20 against the skin of the user. After collection of the sample, the microsampler 12 is retracted to perform the measurement. Such lancing movement is driven by means of the metallic hook 34 which is guided by the plastic material of the holding unit 16 surrounding the oblong hole 32, thereby preventing wear by avoiding a metal-to-metal contact.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A sampling device for collecting a body fluid sample, comprising:
   a metal lancing unit having a distal tip configured for piercing skin and a capillary channel extending between the tip and a proximal section of the lancing unit for collecting body fluid;

a plastic holding unit affixed to the lancing unit and configured for manipulating the lancing unit to form an incision in the skin;

a test pad supported between the plastic holding unit and the lancing unit, the test pad contacting the lancing unit; and the holding unit containing a sorbent adapted for sorption of moisture and/or volatile substances to protect the sampling device from degradation prior to use.

2. The sampling device of claim 1, wherein the sorbent is selected from the group consisting of carbon black, activated carbon, graphite, desiccant polymers, silica gel, zeolites, ion exchange resins, molecular sieve materials.

3. The sampling device of claim 1, wherein the sorbent is dispersed in the plastic material of the holding unit or disposed therein or coated thereon.

4. The sampling device of claim 1, wherein the holding unit is formed from an injection molded component from a molding composition containing the sorbent.

5. The sampling device of claim 1, wherein the holding unit comprises a plastic structure adapted for releasable engagement of an actuation mechanism.

6. The sampling device of claim 5, wherein the holding unit has a hole or a recess.

7. The sampling device of claim 1, wherein the lancing unit comprises an elongate piece of a flat material.

8. The sampling device of claim 7, wherein the lancing unit is formed from a sheet of stainless steel.

9. The sampling device of claim 1, wherein the capillary channel comprises a groove or slit which is laterally open to the outside on one side or on two opposite sides.

10. The sampling device of claim 1, wherein the test paid is adapted for detecting at least one analyte in the body fluid and arranged to receive body fluid via the capillary channel.

11. The sampling device of claim 10, wherein the test paid is in fluidic connection to the capillary channel.

12. The sampling device of claim 10, wherein the test pad is retained on a surface area of the holding unit and the surface area confines a measuring window for an optical detection of the analyte.

13. The sampling device of claim 1, wherein the holding unit is fixedly connected to a proximal part of the lancing unit via form-locked connecting elements.

14. The sampling device of claim 13, wherein the form-locked connecting elements comprise riveted pins.

15. A sampling system for collecting a sample of a body fluid comprising a sampling device according to claim 1 and further comprising an actuator operable to drive a lancing movement of the lancing unit, wherein the actuator comprises a metallic driving member adapted to engage a plastic structure of the holding unit.

16. The sampling system of claim 15, wherein the metallic driving member comprises a gripper or hook.

17. The sampling system of claim 15, wherein the plastic structure has a hole or a recess in the holding unit.

18. The sampling unit of claim 1, wherein the test pad comprises a test chemistry configured for detecting an analyte in the body fluid sample.

19. A sampling device for collecting a body fluid sample, comprising:
a metal lancing unit having a distal tip configured for piercing skin and a capillary channel extending between the tip and a proximal section of the lancing unit for collecting body fluid;
a one-piece plastic holding unit affixed to the lancing unit and configured for manipulating the lancing unit to form an incision in the skin;
a test pad supported between the plastic holding unit and the lancing unit; and
the holding unit containing a sorbent adapted for sorption of moisture and/or volatile substances to protect the sampling device from degradation prior to use.

* * * * *

UNITED STATES PATENT AND TRADEMARK OFFICE
CERTIFICATE OF CORRECTION

| | | |
|---|---|---|
| PATENT NO. | : 10,869,625 B2 | Page 1 of 1 |
| APPLICATION NO. | : 15/717253 | |
| DATED | : December 22, 2020 | |
| INVENTOR(S) | : Wilhelm Leichner | |

It is certified that error appears in the above-identified patent and that said Letters Patent is hereby corrected as shown below:

In the Claims

Column 5, Line 32, Claim 10, the phrase "wherein the test paid" should read --wherein the test pad--.

Column 5, Line 34, Claim 11, the phrase "wherein the test paid" should read --wherein the test pad--.

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*